(12) United States Patent
Jørgensen et al.

(10) Patent No.: US 11,074,690 B2
(45) Date of Patent: Jul. 27, 2021

(54) METHOD FOR ENHANCING THE VISIBILITY OF BLOOD VESSELS IN COLOR IMAGES AND VISUALIZATION SYSTEMS IMPLEMENTING THE METHOD

(71) Applicant: AMBU A/S, Ballerup (DK)

(72) Inventors: Andreas Härstedt Jørgensen, Rødovre (DK); Finn Sønnenborg, Frederikssund (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 16/811,927

(22) Filed: Mar. 6, 2020

(65) Prior Publication Data

US 2020/0211190 A1    Jul. 2, 2020

Related U.S. Application Data

(63) Continuation-in-part of application No. PCT/EP2019/073483, filed on Sep. 3, 2019.

(30) Foreign Application Priority Data

Sep. 7, 2018 (EP) .................................... 18193186

(51) Int. Cl.
*G06T 7/00* (2017.01)
*G06T 1/20* (2006.01)
*G06T 5/50* (2006.01)

(52) U.S. Cl.
CPC .............. *G06T 7/0012* (2013.01); *G06T 1/20* (2013.01); *G06T 5/50* (2013.01); *G06T 2200/24* (2013.01);
(Continued)

(58) Field of Classification Search
CPC ..... A61B 1/00009; A61B 1/05; G06T 7/0012; G06T 2207/30101; G06T 7/90;
(Continued)

(56) References Cited

U.S. PATENT DOCUMENTS

| 4,583,027 A | 4/1986 | Parker |
| 5,942,817 A | 8/1999 | Chitayat |

(Continued)

FOREIGN PATENT DOCUMENTS

| EP | 2474265 A2 | 7/2012 |
| EP | 3 123 927 A1 | 2/2017 |

(Continued)

OTHER PUBLICATIONS

International Search Report and Written opinion in related International Application No. PCT/EP2019/073483, dated Nov. 28, 2019; 5 pages.

(Continued)

*Primary Examiner* — Li Liu
(74) *Attorney, Agent, or Firm* — Faegre Drinker Biddle & Reath LLP

(57) ABSTRACT

A method of enhancing the visibility of blood vessels in a colour image captured by an image capturing device of a medical device, including, for at least some of the pixels of the image, the steps of: (a) processing data obtained from a first colour channel together with data obtained from a second colour channel to determine a value of a first parameter indicative of the intensity in the red spectrum relative to the total intensity of said pixel; (b) using said value of said first parameter and a first value of a user parameter to alter said pixel, the first value of the user parameter being based on user input, and wherein the strength of the alteration is dependent on both the value of said first parameter and the first value of said user parameter.

20 Claims, 8 Drawing Sheets

(52) U.S. Cl.
CPC .............. *G06T 2207/10016* (2013.01); *G06T 2207/10024* (2013.01); *G06T 2207/20024* (2013.01); *G06T 2207/20081* (2013.01); *G06T 2207/20084* (2013.01); *G06T 2207/20172* (2013.01); *G06T 2207/20224* (2013.01); *G06T 2207/30101* (2013.01)

(58) Field of Classification Search
CPC . G06T 2207/10024; G06T 2207/10068; G06T 2200/24; G06T 2207/20172; G06K 2209/05
See application file for complete search history.

(56) References Cited

U.S. PATENT DOCUMENTS

| | | | |
|---|---|---|---|
| 6,956,602 | B2 | 10/2005 | Higuchi et al. |
| 9,854,962 | B2 | 1/2018 | McGrail et al. |
| 10,321,804 | B2 | 6/2019 | Jacobsen et al. |
| 10,406,309 | B2 | 9/2019 | Daher |
| 10,478,054 | B2 | 11/2019 | Nave et al. |
| 2003/0071895 | A1 | 4/2003 | Higuchi et al. |
| 2012/0179050 | A1* | 7/2012 | Saito .................... A61B 1/0638 600/476 |
| 2014/0316283 | A1 | 10/2014 | Kaku et al. |
| 2016/0239965 | A1 | 8/2016 | Kuramoto |
| 2017/0014021 | A1* | 1/2017 | Kuramoto ............ A61B 1/0684 |
| 2017/0330320 | A1* | 11/2017 | Lynch .................... A61B 5/055 |
| 2018/0068437 | A1 | 3/2018 | Bronkalla et al. |

FOREIGN PATENT DOCUMENTS

| | | |
|---|---|---|
| EP | 3127469 | 2/2017 |
| JP | 2016 174836 | 10/2016 |

OTHER PUBLICATIONS

Golhar, Mayank et al. "Blood Vessel Delineation in Endoscopic Images with Deep Learning Based Scene Classification," Intelligent Virtual Agent, Berlin, pp. 147-168, Jun. 16, 2018.
Search Report issued by the European Patent Office dated Nov. 19, 2020 in related European Application No. 18193186.6; 5 pages.
Communication under Rule 71(3), Intention to Grant, issued in EP 18 193 186.6, dated May 27, 2021, 33 pages.

* cited by examiner

METHOD FOR ENHANCING THE VISIBILITY OF BLOOD VESSELS IN COLOR IMAGES AND VISUALIZATION SYSTEMS IMPLEMENTING THE METHOD

The present application is a continuation-in-part of International Application No. PCT/EP2019/073483, filed Sep. 3, 2019, which claims priority from European Application No. 18193186, filed Sep. 7, 2018; said applications are incorporated herein by reference in their entirety.

TECHNICAL FIELD

The disclosure relates to visualization systems including videoscopes with image sensors to capture images of patients. More specifically, the disclosure relates to a method of enhancing the visibility of blood vessels in color images captured by the image sensors, a method for identifying vascular structures, and a visualization system to implement the method.

BACKGROUND OF THE DISCLOSURE

Medical videoscopes comprise endoscopes, colonoscopes, ear-nose-throat scopes, duodenoscopes, and any other medical device having an image sensor configured to obtain images of views of a patient. The term "patient" herein includes humans and animals. Portable medical monitors can be communicatively coupled to the medical videoscopes to receive image data therefrom and present images corresponding to the image data on a display module of the monitor.

Videoscopes are made for various procedures and may have different technical characteristics suited for the procedure they are designed to perform, based on the age of the device, or for other reasons. An endoscope is a type of a videoscope. FIG. 1 is a perspective view of a videoscope, e.g. endoscope 100 comprising a handle 102 with an articulation lever 110 and an insertion tube 104 having a proximal end and a distal end. An articulation tube 106 having an image sensor 109 is disposed at distal end 108 of the articulation tube. The image sensor captures optical images and transmits image data corresponding to the images via a cable 114 to a connector 116. Connector 116 is insertable into a connector port of a monitor to present graphical images corresponding to the optical images with a display module of the monitor. Movement of articulation lever 110 reorients the field of view of image sensor 109. A suction control 112 and an actuator 118 may also be provided.

Another endoscope, described in commonly owned U.S. Patent Application No. 2019/0223694, has an insertion tube with an internal working channel and a connector at the handle adapted for the attachment of a syringe. A recess is adapted to accommodate a cylindrical body of the syringe when the syringe is attached to the connector. The endoscope is adapted to perform bronchioalveolar lavage, a procedure for obtaining samples, through the working channel, of organic material from a lung segment of a patient.

A videoscope can also comprise a endobronchial tube with an image sensor, as described in commonly owned U.S. Pat. Nos. 10,321,804 and 10,406,309. The endobronchial tube comprises a tube having a wall, a first inflatable cuff, a second lumen having an open distal end, a second inflatable cuff, a dedicated image sensor lumen in the wall, an image sensor, and an illumination source within the dedicated image sensor lumen at the distal end thereof. The endobronchial tube may include a dedicated cleaning nozzle arrangement embedded in the wall of the tube.

A videoscope can also comprise a endotracheal tube with an image sensor, as described in commonly owned U.S. Pat. No. 10,478,054. The endotracheal tube comprises a tube having a wall defining a ventilation lumen, an image sensor, and an illumination source within a dedicated image sensor lumen at the distal end of the endotracheal tube.

A videoscope can also comprise a video laryngoscope, as described in commonly owned U.S. Pat. No. 9,854,962, known as the King Vision™ aBlade Video Laryngoscope. The video laryngoscope includes a housing including a display screen, a battery compartment, and a blade. The blade includes an open channel provided to guide insertion of an endotracheal tube. An image sensor is positioned at a distal end of the blade. The image sensor can be part of the blade or can be connected to the housing and introduced into a cavity of a disposable blade.

Videoscopes can be used to guide insertion of other medical devices, such as endotracheal tubes and tools used to collect tissue or fluid samples. Physicians may also utilize images obtained with the videoscopes to analyze tissues and body structures. For example, changes in the vascular structure of internal cavities may be indicative of a number of diseases, such as autoimmune diseases and cancers. However, it may be difficult for medical personnel to correctly and precisely analyse the vascular structures since the blood vessels may blend in with the surrounding tissue types.

The visibility of the blood vessels may be improved by providing the medical device with an additional light source emitting light with a narrow wavelength that is selected so that blood vessels have a high absorption of the light relative to the surrounding tissue. This will, however, increase the cost of the medical device and furthermore change the colors of the resulting image. The change in the colors may make it more difficult for medical personnel to navigate the medical device and, furthermore, more difficult to examine changes in other tissue types of the internal cavities that may be indicative of a pathological condition.

U.S. Pat. No. 6,956,602 discloses an apparatus that includes a level adjusting circuit that increases a gain of a G (or B) signal output from a color conversion circuit, a binarization circuit that forms a binarized image from this G signal, and an edge detection circuit that extracts blood vessel position signals through edge detection based on this binarized signal. Then, the apparatus extracts RGB color signals making up a blood vessel image by using the above-described blood vessel position signals, increases the gains of these blood vessel color signals and then adds the blood vessel color signals to the color signals of an original image. It may, however, be difficult to precisely determine the location of the blood vessels in the image. Thus, areas of the image originating from blood vessels may not be enhanced whereas areas of the images not originating from blood vessels may be enhanced.

Thus, it remains a problem to provide an improved method/device/system for enhancing the visibility of desired color-distinguishable structures, such as blood vessels, in color images recorded by an image sensor of a videoscope.

SUMMARY OF THE DISCLOSURE

According to a first aspect, the present disclosure relates to a method of enhancing the visibility of blood vessels in a color image captured by an image capturing device of a medical device, said color image having a plurality of color channels and having a plurality of pixels, wherein said method comprises for at least some of said plurality of pixels the steps of: (a) processing data obtained from a first color channel together with data obtained from a second color channel to determine a value of a first parameter indicative of the intensity in the red spectrum relative to the total intensity of said pixel; and (b) using said value of said first parameter and a first value of a user parameter to alter said pixel, the first value of the user parameter being based on user input, and wherein the strength of the alteration is dependent on both the value of said first parameter and the first value of said user parameter.

Consequently, a user may control the strength of the enhancement to adapt the enhancement to a specific situation. Furthermore, by using information from at least two color channels more information in the color image may be used to estimate the location of the blood vessels allowing a more precise estimate.

In some embodiments, the user parameter has at least three possible value e.g. the user may select 'low' enhancement, 'medium' enhancement and 'high' enhancement. The user parameter may have more than three possible values, whereby the user may select the strength of the enhancement on a sliding scale with 'low' enhancement at one end of the scale and 'high' enhancement at another end of the scale.

The user input may be an input from one or more buttons provided in connection with the medical device e.g. if the medical device is an endoscope, the user input may be from one or more buttons arranged in connection with the endoscope handle e.g. on the endoscope handle. As an example, the endoscope handle may be provided with a first button for increasing the strength of the enhancement and a second button for decreasing the strength of the enhancement. Alternatively, the endoscope handle may be provided with a single button for selecting the strength of the enhancement e.g. a first activation of the button may select 'low' enhancement, a second activation may select 'medium' enhancement, a third activation may select 'high' enhancement, and a fourth activation may again select 'low' enhancement and so forth. A button of the one or more buttons may be used to activate/deactivate the enhancement e.g. if only a single button is provided the single button may also activate/deactivate the enhancement.

The user input may alternatively/additionally be an input from one or more buttons provided in connection with a monitor for displaying images obtained by the image capturing device. The one or more buttons may be arranged in proximity of the screen of the monitor e.g. at the display frame.

Additionally/alternatively the screen of the monitor may be a touch-screen whereby the user input may be an input from the touch-screen e.g. a virtual button on the touch-screen and/or a slider on the. The monitor may be configured to be in a first state and a second state where when the monitor is in the first state the touch-screen displays a first user interface allowing the user to turn on the enhancement and/or change the strength of the enhancement, and when the monitor is in the second state display a second user interface allowing the user to alter other imaging parameter and/or use a larger portion of the display surface for displaying live images.

In some embodiments, whenever the enhancement is activated a visual identifier such as a symbol or icon is inserted into the enhanced image to show that the image has been enhanced.

In some embodiment, the method further comprises storing a first enhanced image; storing an original un-enhanced image or image data capable of re-creating the original un-enhanced image based on the stored enhanced image; obtaining a second value of the user parameter based on user input; and creating a second enhanced image based on the original un-enhanced image and the second value of the user parameter, the second enhanced image being enhanced with a different strength than the first enhanced image.

Consequently, a user may turn off the enhancement on a captured and stored image and/or change the strength of the enhancement.

The user input may be received from one or more buttons on the medical device and/or on a monitor. The first enhanced image and the original un-enhanced image may be stored responsive to an activation of a shutter-release button e.g. on the medical device or on a monitor. The image data capable of re-creating the original un-enhanced image may be a difference image e.g. obtained by subtracting the enhanced image from the original image and/or a compressed image.

In some embodiments, said first parameter has at least three possible values.

Consequently, by using a non-binary value to determine the degree of alterations a more robust method is provided creating more life-like images.

The medical device may be a medical device adapted to be introduced into a body cavity such as the body cavities of the digestive system or a body cavity of the airways. The medical device may be an elongated rigid or flexible endoscope, a capsule endoscope or laryngoscope. The medical device may comprise one or more light sources configured to emit substantially white light. The medical device may be a single use elongated flexible endoscope. The image capturing device may be arranged at a distal portion of an endoscope e.g. at the tip of an endoscope. The image capturing device may be operatively connectable to an image processor configured to process the image data. Alternatively/additionally, the medical device may comprise an image processor configured to process the image data. The color images may be coded in any color space such as an RGB type color space or an YCbCr type color space. The color images may comprise at least three color channels. The steps of the method e.g. step (a) and step (b) may be performed on the pixels of the color images in parallel e.g. step (a) may be performed for all pixels in the image and then subsequently step (b) may be performed for all pixels in the image. Alternatively, the steps of the method may be performed sequential e.g. step (a) and step (b) may be performed on the pixels of the color images sequential e.g. step (a) and (b) may be performed on a first pixel and then subsequent step (a) and (b) may be performed on a second pixel and so forth. Estimating a value of a first parameter indicative of the intensity in the red spectrum relative to the total intensity has shown to be a good indicator of blood vessels. The value may be a more precise indicator of the intensity in the red spectrum relative to the total intensity if information from all color channels are used, however the value may also be determined using only information from only some color channels e.g. two out of three color channels.

In some embodiments, step (a) comprises: processing data obtained from a first color channel together with data obtained from a second color channel and data obtained from a third color channel to determine a value of said first parameter.

Consequently, by using more data a more precise estimate of the location of the blood vessels may be provided.

In some embodiments, said data obtained from the first color channel is processed together with said data obtained from the second color channel to create a value of a first sub parameter, said data obtained from said first color channel is processed together with said data obtained from said third color channel to create a value of a second sub parameter, and wherein said value of said first sub parameter is processed together with said value of said second sub parameter to create said value of said first parameter.

In some embodiments, said value of said first parameter is created by calculating an average of said value of the first sub parameter and the value of the second sub parameter.

The average may be a weighted average or an unweighted average.

In some embodiments, step (a) comprises subtracting said data obtained from the second color channel from said data obtained from the first color channel.

As an example, if the first color channel represents red and the second color channel represents green then a large output will result when the red component of the pixel is significantly higher than the green component.

Consequently, a simple way of determining a value of a parameter indicative of the intensity in the red spectrum relative to the total intensity of the pixel is provided.

In some embodiments, the first parameter may have at least 8 possible values, 16 possible values or 32 possible values.

Consequently, the alteration of the image may be done effectively without introducing unnatural high frequency elements.

In some embodiments, both said value of said first sub parameter and said value of said second sub parameter are indicative of the intensity in the red spectrum relative to the total intensity of said pixel.

In some embodiments, said value of said first sub parameter is created by subtracting said data obtained from the second color channel from said data obtained from the first color channel, and wherein said value of said second sub parameter is created by subtracting said data obtained from the third color channel from said data obtained from the first color channel.

As an example, if the first color channel represents red, the second color channel represents green, and the third color channel represents blue then the value of both the first sub parameter and the second sub parameter will be large when the red component of the pixel is significantly higher than both the green component and the blue component.

The value of the first parameter may also be determined by calculating a ratio between the data obtained from the first color channel and the sum of the data obtained from the first color channel, the second color channel and/or the third color channel e.g. by dividing the data obtained from the first color channel with the sum of the data obtained from the first color channel, the second color channel and/or the third color channel.

In some embodiments, parts of the color image having no blood vessels are substantially unaltered and displayed with normal colors.

In some embodiments, step (b) comprises subtracting or adding a value of an alteration parameter from the value of at least one color channel of the plurality of color channels of said color image, wherein the value of the alteration parameter is related to the value of the first parameter.

The value of the alteration parameter may simply be the value of the first parameter. The alteration parameter may be subtracted from all color channels of said color image.

In some embodiments, said method further comprises determining a value of a second parameter indicative of the intensity of said pixel and wherein said value of said first parameter together with said value of said second parameter is used to alter said pixel.

This may allow the method to decrease the strength of the alterations in dark areas of the color image, where noise may make it difficult to precisely determine blood vessel locations.

In some embodiments, said plurality of color channels are normalized prior to being processed together.

In some embodiments, a low pass filtered image is created for each of said plurality of color channels indicating a local average for each pixel, and wherein each color channel is normalized using its low pass filtered image.

In some embodiments, said color image is an RGB color image said first color channel being the red color channel and said second color channel being the green or blue color channel.

In some embodiments, said medical device is configured to be inserted into a body cavity and illuminate said body cavity with white light when said color image is being recorded.

In some embodiments, said medical device is an endoscope.

In some embodiments, a high value of the first parameter indicates a high intensity in the red spectrum relative to the total intensity of said pixel and a low value of the first parameter indicates a low intensity in the red spectrum relative to the total intensity of said pixel.

In some embodiments, values of the first parameter that are among the 50% highest of all possible values results in alterations that are more significant than the alterations that results from values of the first parameter that are among the 50% lowest of all possible values.

In some embodiments, for at least 50% of the possible values of said first parameter an increase in the value of the first parameter results in an increase in the strength of the alteration.

In some embodiments, the alteration of said pixel is independent of the intensity in the green spectrum relative to the blue spectrum.

According to a second aspect, the present disclosure relates to an image processor for enhancing the visibility of blood vessels in a color image, said image processor comprising a processing unit operationally connectable to an image capturing device of a medical device, wherein said processing unit is configured to receive a color image having a plurality of color channels from said image capturing device, said color image has a plurality of pixels, and said processing unit further is configured to for at least some of said plurality of pixels (a) process data obtained from a first color channel together with data obtained from a second color channel to determine a value of a first parameter indicative of the intensity in the red spectrum relative to the total intensity of said pixel; and (b) using said value of said first parameter and a first value of a user parameter to alter said pixel, the first value of the user parameter being based on user input, and wherein the strength of the alteration is dependent on both the value of said first parameter and the first value of said user parameter.

In some embodiments, the user parameter has at least three possible value e.g. the user may select 'low' enhancement, 'medium' enhancement and 'high' enhancement. The user parameter may have more than three possible values, whereby the user may select the strength of the enhancement on a sliding scale with 'low' enhancement at one end of the scale and 'high' enhancement at another end of the scale.

The user input may be an input from one or more buttons operationally connectable to the processing unit provided in connection with the medical device e.g. if the medical device is an endoscope, the user input may be from one or more buttons arranged in connection with the endoscope handle e.g. on the endoscope handle. As an example, the endoscope handle may be provided with a first button for increasing the strength of the enhancement and a second button for decreasing the strength of the enhancement. Alternatively, the endoscope handle may be provided with a single button for selecting the strength of the enhancement e.g. a first activation of the button may select 'low' enhancement, a second activation may select 'medium' enhancement, a third activation may select 'high' enhancement, and a fourth activation may again select 'low' enhancement and so forth. A button of the one or more buttons may be used to activate/deactivate the enhancement e.g. if only a single button is provided the single button may also activate/deactivate the enhancement.

The user input may alternatively/additionally be an input from one or more buttons operationally connectable to the processing unit provided in connection with a monitor for displaying images obtained by the image capturing device. The image processor may be part of the monitor or connectable to the monitor. The one or more buttons may be arranged in proximity of the screen of the monitor e.g. at the display frame.

Alternatively/additionally the screen of the monitor may be a touch-screen operationally connectable to the processing unit whereby the user input may be an input from the touch-screen e.g. a virtual button on the touch-screen and/or a slider on the touch-screen or the like. The monitor may be configured to be set in a first state and a second state where when the monitor is in the first state the touch-screen displays a first user interface allowing the user to turn on the enhancement and/or change the strength of the enhancement, and when the monitor is in the second state display a second user interface allowing the user to alter other imaging parameter and/or use a larger portion of the display surface for displaying live images.

In some embodiments, the processing unit is further configured to insert a visual identifier such as a symbol or icon is inserted into the enhanced image to show to the user that the image has been enhanced when the enhanced image is displayed.

In some embodiment, the processing unit is operationally connectable to a storage unit and further configured to store on the storage unit a first enhanced image; store on the storage unit an original un-enhanced image or image data capable of re-creating the original un-enhanced image based on the stored enhanced image; obtained a second value of a user parameter based on user input; and create a second enhanced image based on the original un-enhanced image and the second value of the user parameter, the second enhanced image being enhanced with a different strength than the first enhanced image.

Consequently, a user may change the strength of the enhancement on recorded images.

The user input may be received from one or more buttons on the medical device and/or on a monitor operationally connectable to the processing unit. The processing unit may be configured to store the first enhanced image and the original un-enhanced image responsive to an activation of a shutter-release button e.g. on the medical device or on a monitor. The processing unit may be operationally connectable to a monitor and configured to allow a user to control the monitor to display the first enhanced image, the second enhanced image, or the original un-enhanced image. The image data capable of re-creating the original un-enhanced image may be a difference image obtained by subtracting the enhanced image from the original image or vice versa and/or a compressed image.

In some embodiments, said first parameter has at least three possible values.

In some embodiments, step (a) comprises: processing data obtained from a first color channel together with data obtained from a second color channel and data obtained from a third color channel to determine a value of said first parameter.

In some embodiments, said data obtained from the first color channel is processed together with said data obtained from the second color channel to create a value of a first sub parameter, said data obtained from said first color channel is processed together with said data obtained from said third color channel to create a value of a second sub parameter, and wherein said value of said first sub parameter is processed together with said value of said second sub parameter to create said value of said first parameter.

In some embodiments, said value of said first parameter is created by calculating an average of said value of the first sub parameter and the value of the second sub parameter.

In some embodiments step (a) comprises subtracting said data obtained from the second color channel from said data obtained from the first color channel.

In some embodiments, the first parameter may have at least 8 possible values, 16 possible values or 32 possible values.

In some embodiments, both said value of said first sub parameter and said value of said second sub parameter are indicative of the intensity in the red spectrum relative to the total intensity of said pixel.

In some embodiments, said value of said first sub parameter is created by subtracting said data obtained from the second color channel from said data obtained from the first color channel, and wherein said value of said second sub parameter is created by subtracting said data obtained from the third color channel from said data obtained from the first color channel.

In some embodiments, parts of the color image having no blood vessels are substantially unaltered and displayed with normal colors.

In some embodiments, step (b) comprises subtracting or adding a value of an alteration parameter from the value of at least one color channel of the plurality of color channels of said color image, wherein the value of the alteration parameter is related to the value of the first parameter.

In some embodiments, said processing unit is further configured to: determine a value of a second parameter indicative of the intensity of said pixel and wherein said value of said first parameter together with said value of said second parameter are used to alter said pixel.

In some embodiments, said plurality of color channels are normalized prior to being processed together.

In some embodiments, a low pass filtered image is created for each of said plurality of color channels indicate a local average for each pixel, and wherein each color channel is normalized using its low pass filtered image.

In some embodiments, said value of said first sub parameter is created by subtracting said data obtained from the second color channel from said data obtained from the first color channel, and wherein said value of said second sub parameter is created by subtracting said data obtained from the third color channel from said data obtained from the first color channel.

In some embodiments, said color image is a RGB color image said first color channel being the red color channel and said second color channel being the green or blue color channel.

In some embodiments, said medical device is configured to be inserted into a body cavity and illuminate said body cavity with white light when said color images are being recorded.

In some embodiments, said medical device is an endoscope.

In some embodiments, a high value of the first parameter indicates a high intensity in the red spectrum relative to the total intensity of said pixel and a low value of the first parameter indicates a low intensity in the red spectrum relative to the total intensity of said pixel.

In some embodiments, values of the first parameter that are among the 50% highest of all possible values results in alterations that are more significant than the alterations that results from values of the first parameter that are among the 50% lowest of all possible values.

In some embodiments, for at least 50% of the possible values of said first parameter an increase in the value of the first parameter results in an increase in the strength of the alteration.

In some embodiments, the alteration of said pixel is independent of the intensity in the green spectrum relative to the blue spectrum.

According to a third aspect the present disclosure relates to an image processor for identifying potential pathological vascular structures, said image processor comprising a processing unit operationally connectable to an image capturing device of a medical device, wherein said processing unit is configured to process an image adapted for computer image analysis using a machine learning data architecture trained to identify potential pathological vascular structures in such images, wherein said image adapted for computer analysis is generated by processing a color image having a plurality of color channels recorded by said image capturing device, said color image has a plurality of pixels wherein the processing of said color image comprises for at least some of said plurality of pixels (a) process data obtained from a first color channel together with data obtained from a second color channel to determine a value of a first parameter indicative of the intensity in the red spectrum relative to the total intensity of said pixel; and (b) using said value of said first parameter to create a pixel value of the image adapted for computer image analysis.

Consequently, by pre-processing the color images using steps a) and b) the vascular structures may be enhanced making it easier for the machine learning data architecture to identify potential pathological vascular structures. This may both enable the machine learning data architecture to identify more potential pathological vascular structures and perform its processing faster, i.e. using fewer computational resources enabling real time analysis by the machine learning data architecture.

In some embodiments, said machine learning data architecture is a supervised machine learning architecture, trained by being provided with a training data set of images created by steps a) and b), where a first subset of images of said training data set show a pathological vascular structure and a second subset of images of said training data set show a healthy vascular structure.

In some embodiments, the training data set comprises a plurality of images showing vascular structures of tumours.

The plurality of images may be recorded by an image capturing device of a medical device such as an endoscope.

In some embodiments, the pixel values of the image adapted for computer image analysis corresponds to the value of the first parameter optionally multiplied with a weight value derived from said color image; or the pixel values of the image adapted for computer image analysis is an altered pixel from said color image altered using the value of said first parameter and wherein the strength of the alteration is dependent on the value of said first parameter.

In some embodiments, said data obtained from the first color channel is processed together with said data obtained from the second color channel to create a value of a first sub parameter, said data obtained from said first color channel is processed together with said data obtained from said third color channel to create a value of a second sub parameter, and wherein said value of said first sub parameter is processed together with said value of said second sub parameter to create said value of said first parameter.

In some embodiments, said value of said first parameter is created by calculating an average of said value of the first sub parameter and the value of the second sub parameter.

In some embodiments step (a) comprises subtracting said data obtained from the second color channel from said data obtained from the first color channel.

In some embodiments, the first parameter may have at least 8 possible values, 16 possible values or 32 possible values.

In some embodiments, both said value of said first sub parameter and said value of said second sub parameter are indicative of the intensity in the red spectrum relative to the total intensity of said pixel.

In some embodiments, said value of said first sub parameter is created by subtracting said data obtained from the second color channel from said data obtained from the first color channel, and wherein said value of said second sub parameter is created by subtracting said data obtained from the third color channel from said data obtained from the first color channel.

In some embodiments, said processing unit is further configured to: determine a value of a second parameter indicative of the intensity of said pixel and wherein said value of said first parameter together with said value of said second parameter are used to create said pixel value of the image adapted for computer image analysis.

In some embodiments, said plurality of color channels are normalized prior to being processed together.

In some embodiments, a low pass filtered image is created for each of said plurality of color channels indicate a local average for each pixel, and wherein each color channel is normalized using its low pass filtered image.

In some embodiments, said value of said first sub parameter is created by subtracting said data obtained from the second color channel from said data obtained from the first color channel, and wherein said value of said second sub parameter is created by subtracting said data obtained from the third color channel from said data obtained from the first color channel.

In some embodiments, said color image is a RGB color image said first color channel being the red color channel and said second color channel being the green or blue color channel.

In some embodiments, a high value of the first parameter indicates a high intensity in the red spectrum relative to the total intensity of said pixel and a low value of the first parameter indicates a low intensity in the red spectrum relative to the total intensity of said pixel.

In some embodiments, values of the first parameter that are among the 50% highest of all possible values results in alterations that are more significant than the alterations that results from values of the first parameter that are among the 50% lowest of all possible values.

In some embodiments, for at least 50% of the possible values of said first parameter an increase in the value of the first parameter results in an increase in the strength of the alteration.

In some embodiments, the alteration of said pixel is independent of the intensity in the green spectrum relative to the blue spectrum.

In some embodiments, the machine learning data architecture is an artificial neural network such as a deep structured learning architecture.

In some embodiments, the processing unit is directly operationally connectable to the image capturing device and configured to receive the color image and perform steps a) and b) to create the image adapted for computer image analysis.

In some embodiments, the processing unit is indirectly operationally connectable to the image capturing device via another image processor.

In some embodiments, said image processor is configured to receive said image adapted for computer image analysis from said another image processor, said another image processor being configured to receive the color image and perform steps a) and b) to create the image adapted for computer image analysis.

According to a fourth aspect, the present disclosure relates to a monitor for displaying images obtained by an image capturing device of a medical device, wherein said monitor comprises an image processor as disclosed in relation to the second aspect of the present disclosure or the third aspect of the present disclosure.

According to a fifth aspect, the present disclosure relates to an endoscope system comprising an endoscope and an image processor as disclosed in relation to the second aspect of the present disclosure or the third aspect of the present disclosure, wherein said endoscope has an image capturing device and said processing unit of said image processor is operationally connectable to said image capturing device of said endoscope.

In some embodiments, the endoscope system further comprises a monitor as disclosed in relation to the fourth aspect of the present disclosure, wherein said monitor is operationally connectable to said image capturing device of said endoscope and configured display said captured images.

According to a sixth aspect the present disclosure relates to a computer program product comprising program code means adapted to cause a data processing system to perform the steps of the method disclosed in relation to the first aspect of the present disclosure, when said program code means are executed on the data processing system.

In some embodiments, said computer program product comprises a non-transitory computer-readable medium having stored thereon the program code means.

According to a seventh aspect the present disclosure relates to a data processing system configured to perform the method disclosed in relation to the first aspect of the present disclosure.

The different aspects of the present disclosure can be implemented in different ways including methods, image processors, monitors, endoscope systems, and compute program products described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependant claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present disclosure, will be further elucidated by the following illustrative and non-limiting detailed description of embodiments of the present disclosure, with reference to the appended drawings, wherein.

In the drawings, corresponding reference characters indicate corresponding parts, functions, and features throughout the several views. The drawings are not necessarily to scale and certain features may be exaggerated in order to better illustrate and explain the disclosed embodiments.

DETAILED DESCRIPTION

Figure 1:
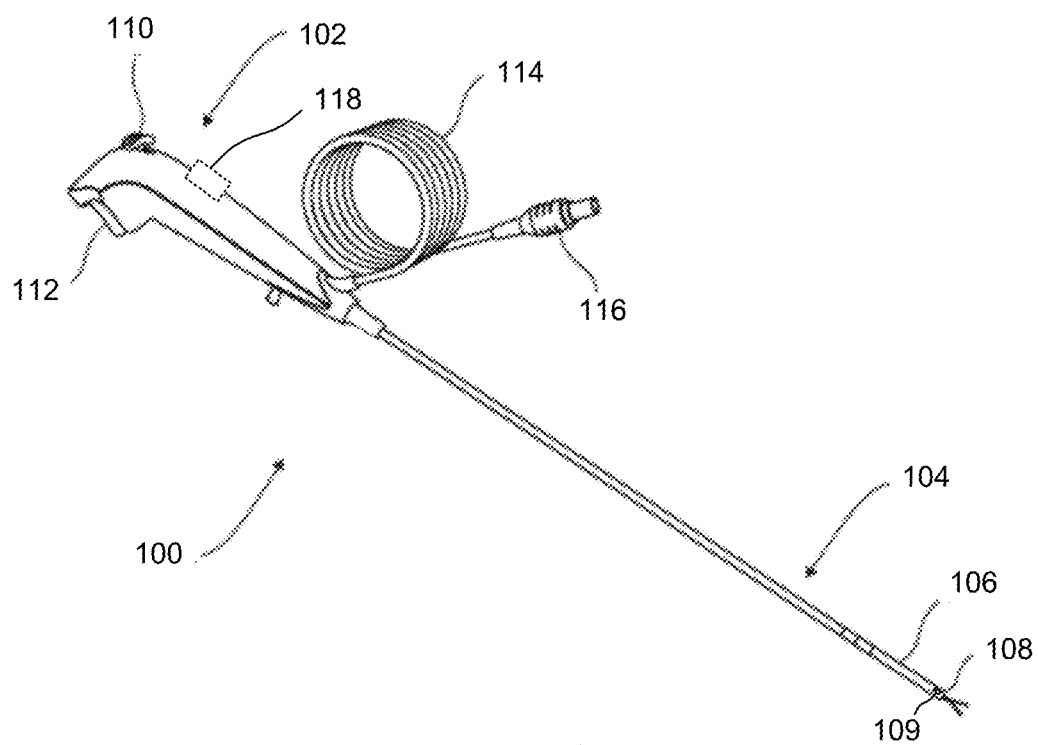
FIG. 1 shows an example of an endoscope.

In the following description, reference is made to the accompanying figures, which show by way of illustration how the embodiments of the present disclosure may be practiced.

Due to the blood light absorption spectrum, blood vessels are more visible in the green and blue components of an RGB image than in the red component. When it is desired to highlight the blood vessels, this characteristic of blood vessels can be used to create, from a base image, a differentiated mass image (e.g. first parameter image) in which the pixels related to the blood vessels, or other structures of interest, stand out relative to the remaining pixels. The differentiated mass image is then combined with the base image to produce an enhanced image in which the blood vessels are darkened relative to the remaining parts of the image.

The differentiated mass image can be generated by processing the red and green components, or the red and blue components, or the red, green and blue components of the color image. Processing all three components is preferrable since the green and blue components provide different information about the blood vessels. It should be understood that the term "mass" refers to a color differentiable mass. Blood vessels are one example of a color differentiable mass. Other examples include bones, scar tissue, organs, foreign objects, etc. The steps to create the differentiated mass image might differ depending on the color characteristics of the color differentiable mass. Thus, the descriptions below made with reference to blood vessels are to illustrate the disclosed image processing methods, which are generally applicable to other types of mass.

The base image can be an original image or an original image that was processed in traditional ways to improve contrast, white balance etc. The original image may be generated by an image sensor including a Bayer filter, in which, as is well known, the filter pattern is 50% green, 25% red, and 25% blue.

Various additional steps can be taken to further improve the display of the blood vessels. In one example, the impact of the red pixels is reduced. The reduction can be accomplished by normalizing the color components, by reducing the intensities of the red pixels, or in other suitable ways. Normalization may be accomplished by low-pass filtering to create low-pass filtered images and then dividing the images by the low-pass filtered images. Reducing the intensities can be accomplished by applying a negative gain to the red pixels or by subtracting a constant value from the red pixels. Red impact reduction may be performed prior to generating the differentiated mass image.

In another example, the impact of the pixels that contain little or no information is reduced. The reduction can be accomplished by setting the intensity of pixels with high (overexposed) or low (underexposed) intensities to 0. Underexposed pixels may reflect tissue far from the tip of the endoscope, thus poorly illuminated. Overexposed pixels may reflect tissue near the light of the endoscope. One way to reduce the impact is to create a mask image by binarizing the pixels. Pixels with intensity in a desired range are assigned a value of 1 and pixels in the undesired intensity range are assigned a value of 0. When the mask image is multiplied by another image, the intensities of the pixels with value of 0 remove the noise provided by the under and over exposed pixels. If the intensities of the pixels range between −1 and +1, for example, as they might in the differentiated mass image, pixels with negative intensities reflect dark areas of the image and their impact is reduced by creating a mask with the positive intensity pixels. The over/under exposure impact can be reduced before or after creating the differentiated mass image.

In a further example, a user may determine the level of enhancement. The level can be selected by the user with an enhancement level selector, and a user selected enhancement amount can then be applied. One way to apply the user selected enhancement amount is to apply a gain value to an image. The image may be the differentiated mass image, before or after application of a mask. The gain value multiplies the intensities of all the pixels by the gain amount. The gain may be in a range between 0-1, where 0 indicates no gain and values between 0-1 indicate an increase of the enhancement up to a maximum value that can be based on the particular videoscope or preset.

Figure 6:
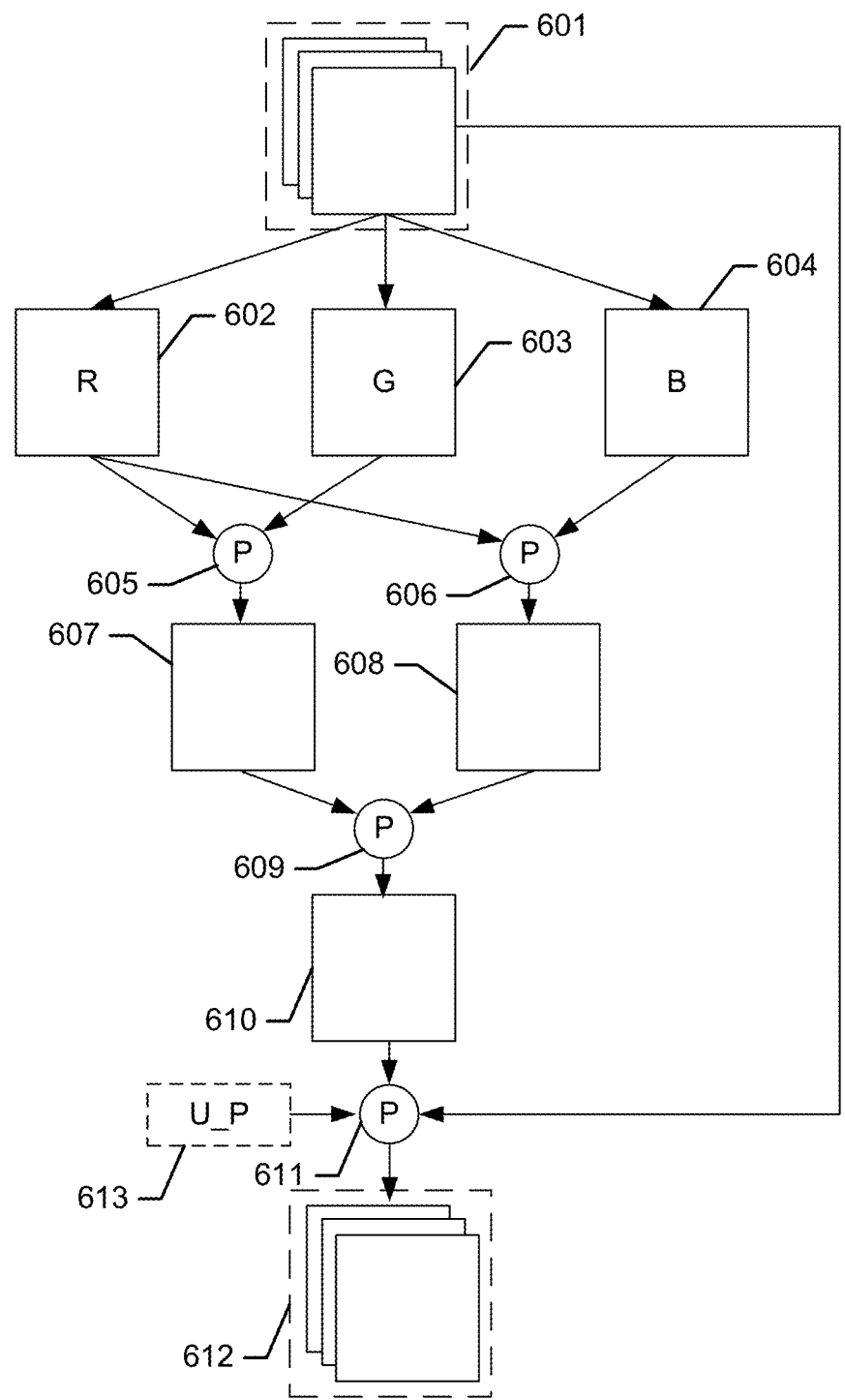
FIG. 6 shows a flow chart of a method of enhancing the visibility of blood vessels in a color image captured by an image capturing device of a medical device according to an embodiment of the disclosure.
Figure 7:
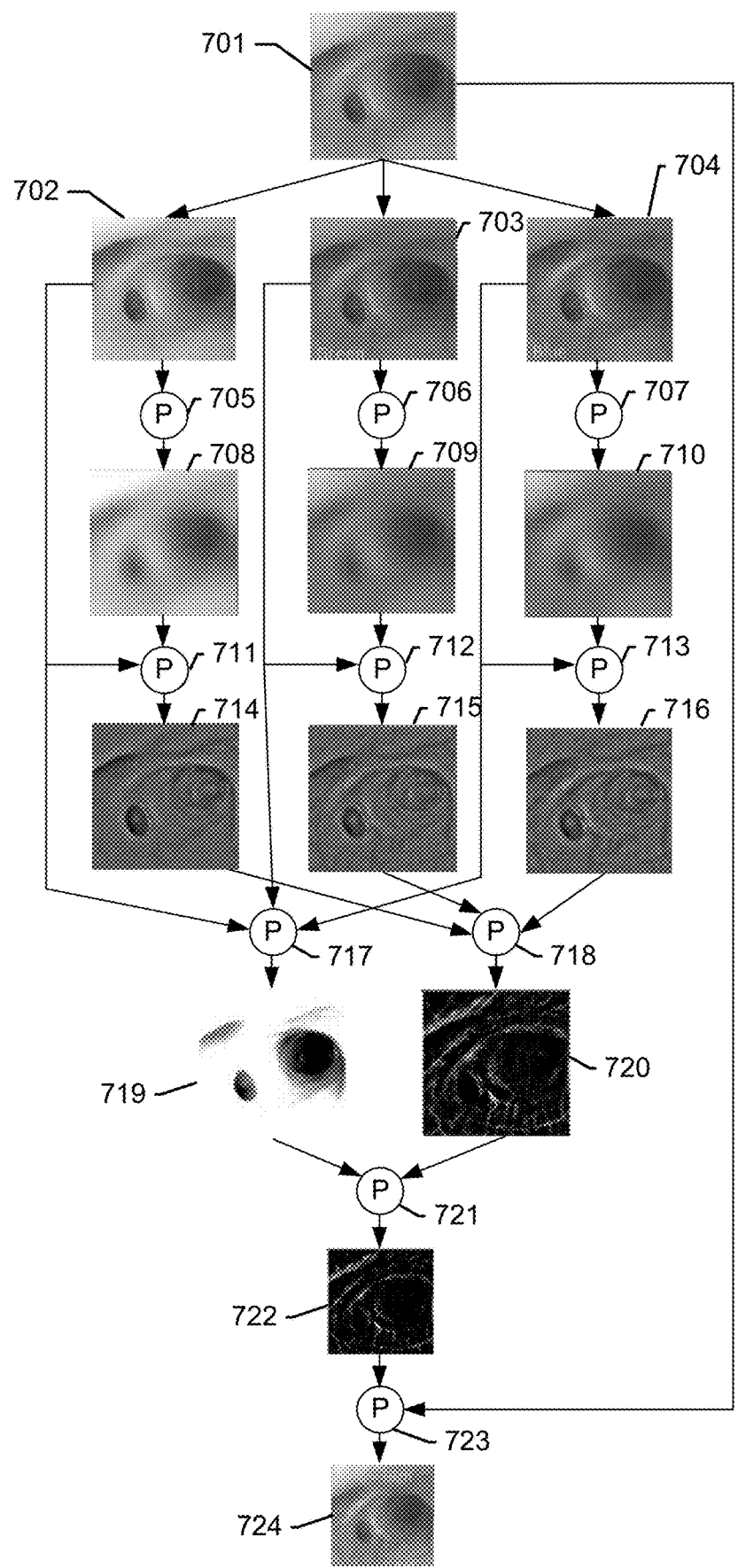
FIG. 7 shows a flow chart of a method of enhancing the visibility of blood vessels in a color image captured by an image capturing device of a medical device according to an embodiment of the disclosure.
Figure 8A:
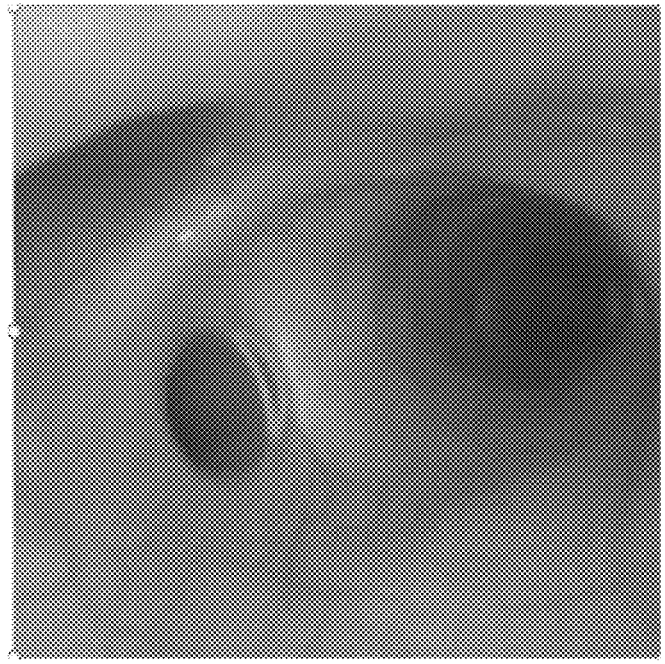
FIG. 8a shows a color image of an internal cavity before the visibility of the blood vessels have been enhanced and FIG. 8b shows the color image after the visibility of the blood vessels have been enhanced according to an embodiment of the disclosure.
Figure 8B:
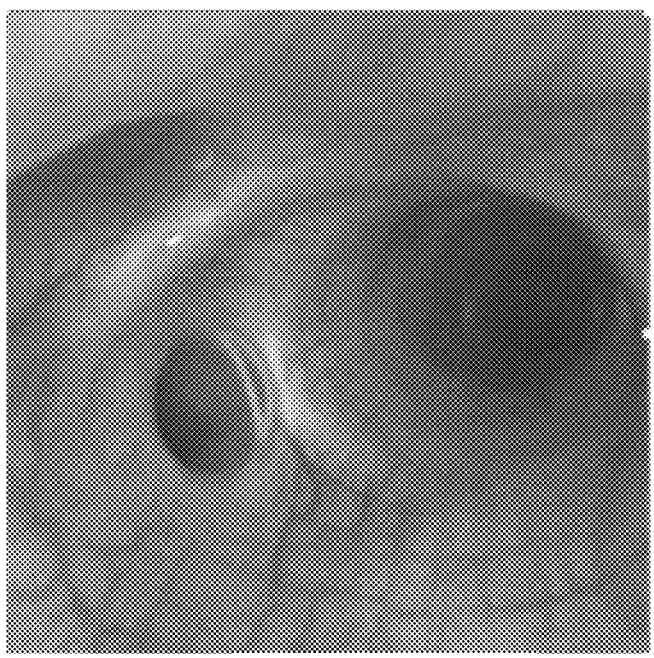
Figure 10:
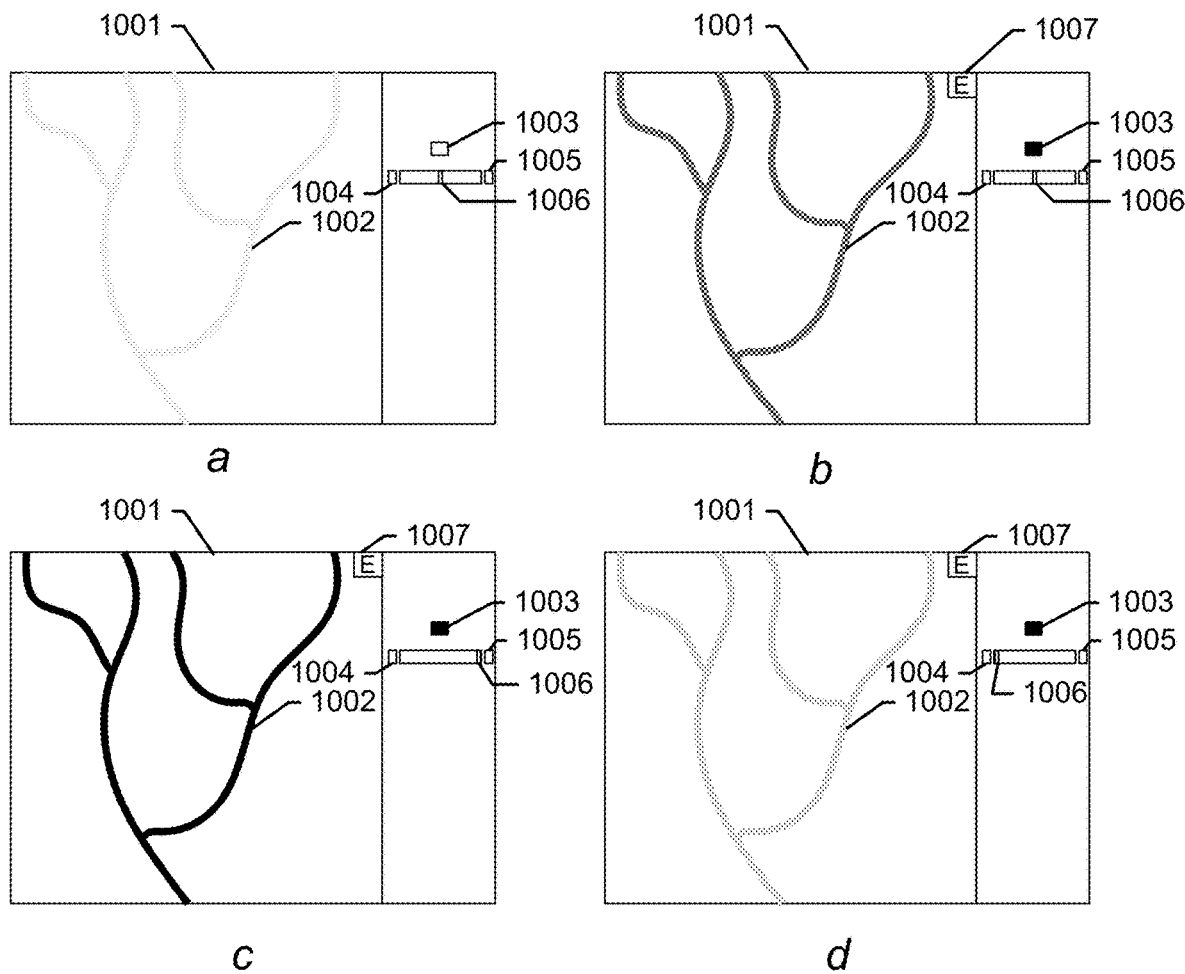
FIG. 10 illustrates how the strength of the enhancement may be controlled using a touch-screen according to an embodiment of the disclosure.
Figure 11:
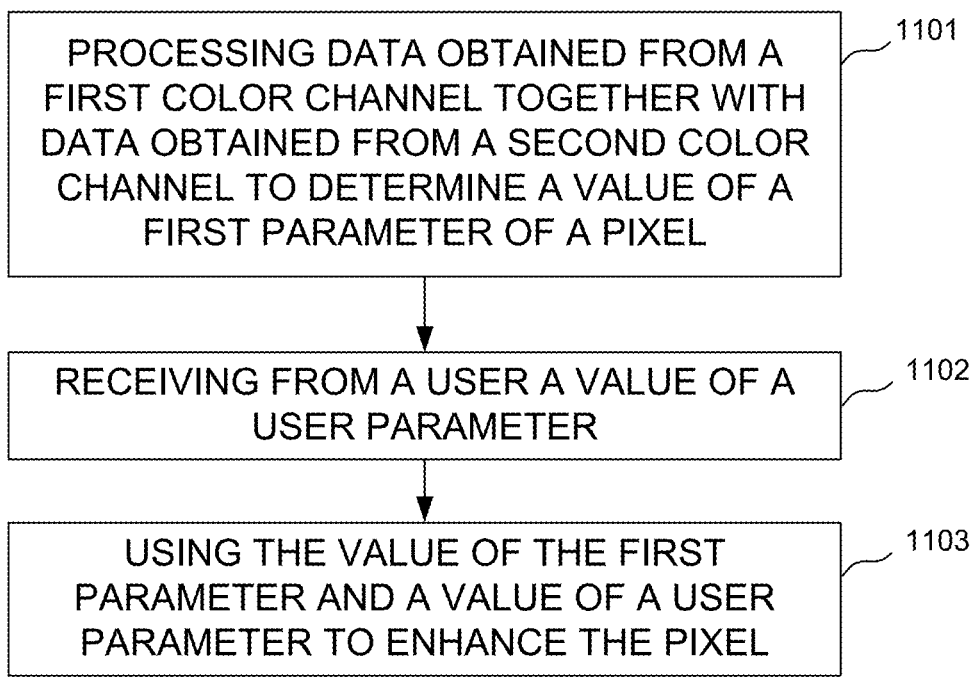
FIG. 11 shows a flow chart of a method of enhancing the visibility of blood vessels in a color image captured by an image capturing device of a medical device according to an embodiment of the disclosure.
Figure 12:
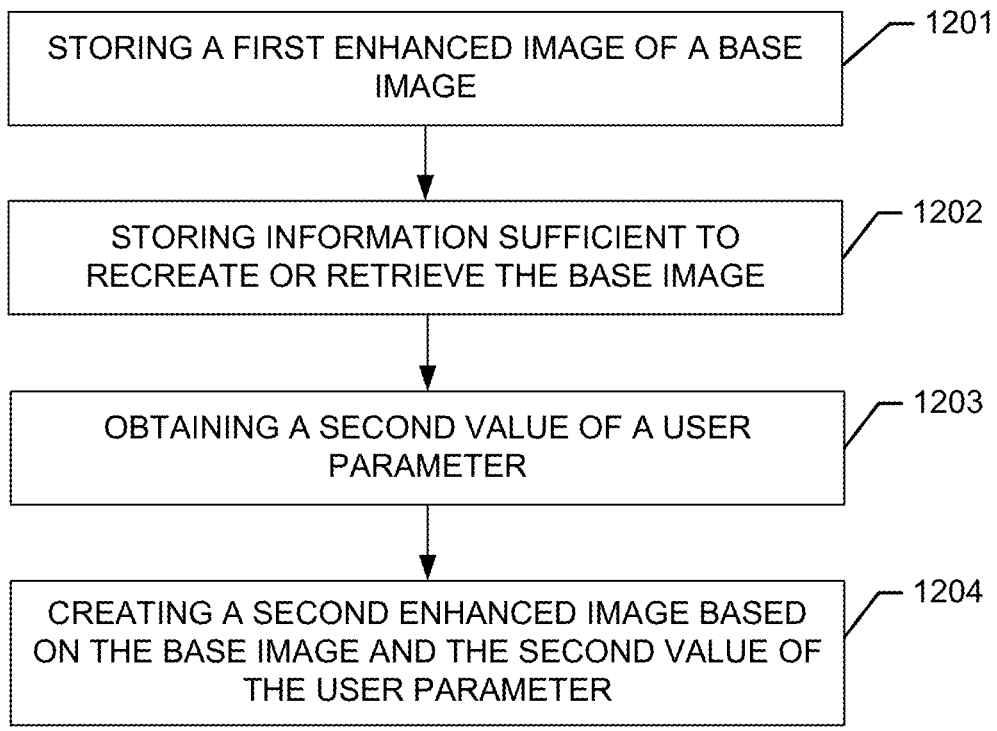
FIG. 12 shows a flow chart of a method according to an embodiment of the disclosure.

In the figures below, detailed embodiments depicting the generation of enhanced images to highlight color differentiable masses are provided. FIGS. 1, 2, 4, 5, and 9 depict embodiments of a visualization system configured to implement the image enhancement method. FIGS. 3, 6 and 7 disclose detailed embodiments of the image enhancement method. FIGS. 8a and 8b contrast an unenhanced image with an enhanced image. FIG. 10 contrasts an un-enhanced image with images enhanced at low, medium, and high enhancement levels selected by the user. FIGS. 11 and 12 disclose embodiments of methods to leverage the enhanced images to identify a mass or structure of interest.

FIG. 1 illustrates an example of an endoscope 100. This endoscope may be adapted for single-use. The endoscope 100 is provided with a handle 102 attached to an insertion tube 104 provided with a bending section 106. The insertion tube 104 as well as the bending section 106 may be provided with one or several working channels such that instruments, such as a gripping device, may be inserted into a human body via the endoscope. One or several exit holes of the one or several channels may be provided in a tip part, or cap, 108 of the endoscope 100. In addition to the exit holes, a camera 109 and one or several light sources, such as light emitting diodes (LEDs), fiber, or any other light emitting devices, may be placed in the tip part 108. The camera may comprise an image sensor, such as a CMOS sensor or any other image capturing device, and one or more lenses defining a field of view of the camera.

The bending section 106 can be bent in different directions with respect to the insertion tube 104 to make it possible for the operator to redirect the camera and obtain different views. The operator can control the bending section 106 with a knob 110 placed on the handle 102. The handle is designed so that the knob 110 can be actuated by a thumb of the operator, but other actuation designs to orient the field of view of the camera are also possible. A push button 112 may be used to control a gripping device or other device provided via a working channel. The handle is designed such that the push button 112 can be actuated by a finger of the operator holding the handle, but other tool actuator designs are also possible.

Figure 2:
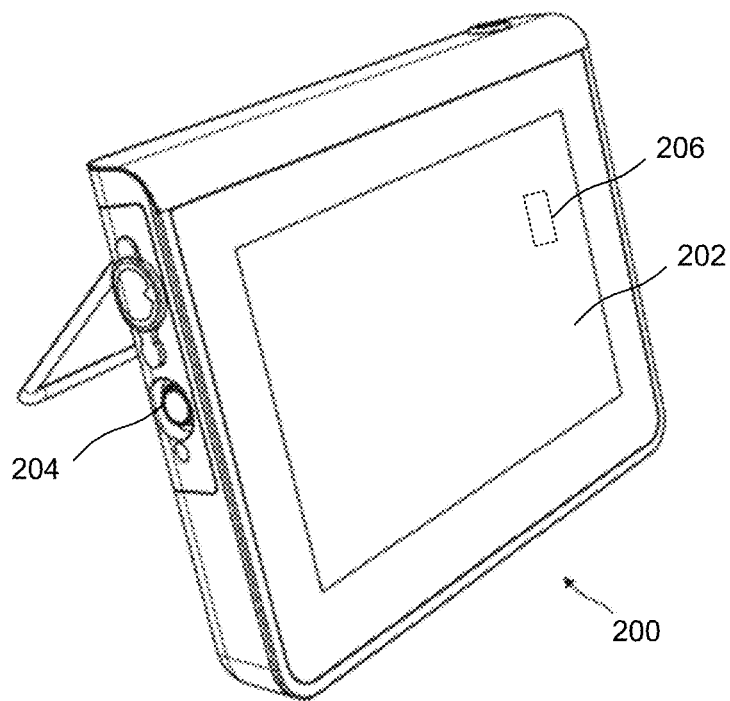
FIG. 2 shows an example of a monitor that can be connected to the endoscope shown in FIG. 1.
Figure 3:
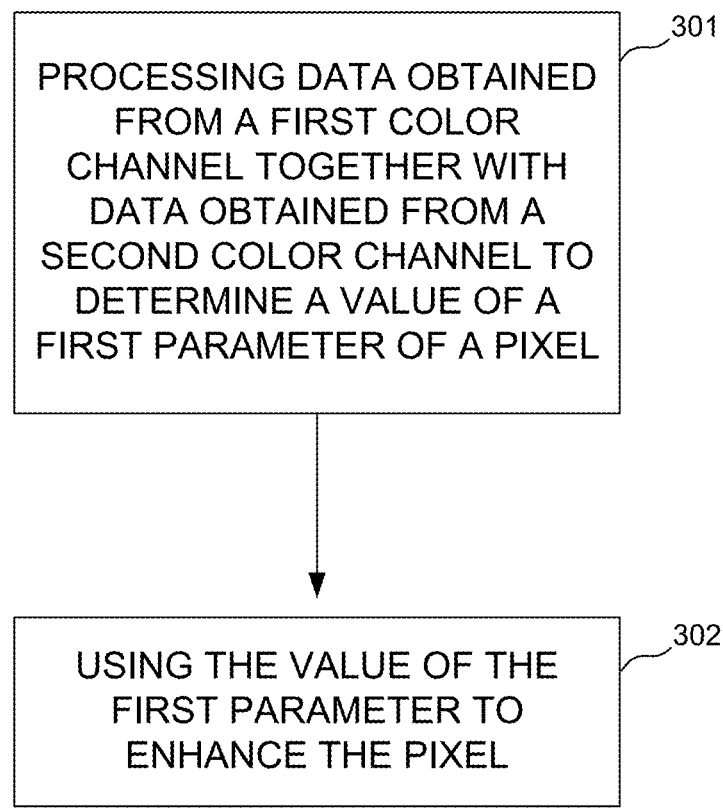
FIG. 3 shows a flow chart of a method of enhancing the visibility of blood vessels in a color image captured by an image capturing device of a medical device according to an embodiment of the disclosure.

The image data captured by the camera and, optionally, other data captured by other sensors, can be transferred via a cable 114 having a connector 116 to a monitor 200, shown in FIG. 2. Even though wire-based data transmission is illustrated, it is equally possible to transfer image data by using a wireless transceiver supported by the endoscope.

An embodiment of a enhancement level selector 118 is shown in schematic form on handle 102. The enhancement level selector will be described in more detail with reference to FIGS. 4 and 5. Generally, the enhancement level selector is an actuator, virtual or physical, operable by the user to generate a signal indicative of a desired mass enhancement level. In one variation, the enhancement level selector includes one or more buttons configured to enable the user to select the video enhancement level. In one example, an enhancement level selector positioned in the handle may include a potentiometer operable by the user to change a resistance indicative of the level of enhancement desired by the user. In another example, an enhancement level selector positioned in the handle may include a potentiometer operable by the user to change a resistance indicative of the level of enhancement desired by the user, and an I²C slave node circuit that includes the ADC and transmits a corresponding value via an existing I²C channel to the monitor, where an I²C master communicates the value of the user parameter to the GUI.

FIG. 2 illustrates an example of a portable monitor 200 including a display screen 202 and a communication port 204 operable to receive the connector 116 of the endoscope 100 to establish communications between the portable monitor 200 and the endoscope 100. The monitor 200 is configured to display images based with the display screen 202 of image data captured by the camera 109 of the endoscope 100. An operator of the endoscope 100 is able to see and analyze an inside of the human body to, for instance, localize a position for taking a sample. In addition, the operator will be able to control the instrument in a precise manner due to the visual feedback made available by the camera 109 and the monitor 200. Further, since some diseases or health issues may result in a shift in natural colors or other visual symptoms, the visual feedback provides the operator valuable input for making a diagnosis based on the image data provided via the camera sensor and the monitor.

The monitor 200 is preferably a re-usable piece of equipment. By having one single-use piece of equipment and another re-usable piece of equipment, most of the data processing capability may be placed in the re-usable piece of equipment in order to reach a cost efficient level at the same time as being safe to use from a health perspective. Single-use devices are not made to withstand sterilization and design considerations include low cost and disposability.

The monitor 200 may comprise an image processor as explained in relation to the second aspect of the disclosure and/or the third aspect of the disclosure. The monitor 200 may be provided with a enhancement level selector 206 described in more detail with reference to FIG. 4. The enhancement level selector 206 may comprise an icon of a graphical user interface (GUI) which the user may actuate to select the desired enhancement level. In other variations, the enhancement level selector 206 may include one or more physical buttons, located on a margin surrounding the display screen or on a side of the monitor, configured to enable a user to select the enhancement level.

As indicated above, the video enhancement highlights masses, or structures, of particular colors. FIG. 3 shows a flowchart of an embodiment of a method for enhancing the visibility of blood vessels in a color image. It should be understood that a color image in this context is comprised of data corresponding to color channels or components. When each color channel is split from the color image, the data can be referred to as a red, green, or blue color image, which is represented by an array comprising pixel data including the respective color information. The method comprises, for at least some of the plurality of pixels, at 301, processing data obtained from a first color channel together with data obtained from a second color channel to determine a value of a first parameter indicative of the intensity in the red spectrum relative to the total intensity of a pixel. At 302, the method continues by using the value of the first parameter to enhance the pixel. The first parameter has at least three possible values, and the strength of the enhancement is dependent on the value of the first parameter.

The first parameters of the pixels form a first image, which may be the differentiated mass image. Processing data obtained from a first color channel together with data obtained from a second color channel to determine a value of a first parameter may comprise obtaining a difference between the red and green, red and blue, or both red/green and red/blue channels. Processing may also comprise reducing the impact of the red pixels, as discussed above, before generating the first, or differentiated mass, image, and neutralizing the impact of over and under exposed pixels. If a user selected enhancement level is applied, processing may also comprise taking the selected enhancement level into account when reducing the impact of the red pixels, for example by reducing the impact more or less depending on the selected enhancement level. The intensity of the processed image can be adjusted to complete the enhanced image, therefore changing the relative intensity of the red pixels to the green or blue or both green and blue pixel intensities changes how dark the blood vessels will appear.

Figure 4:
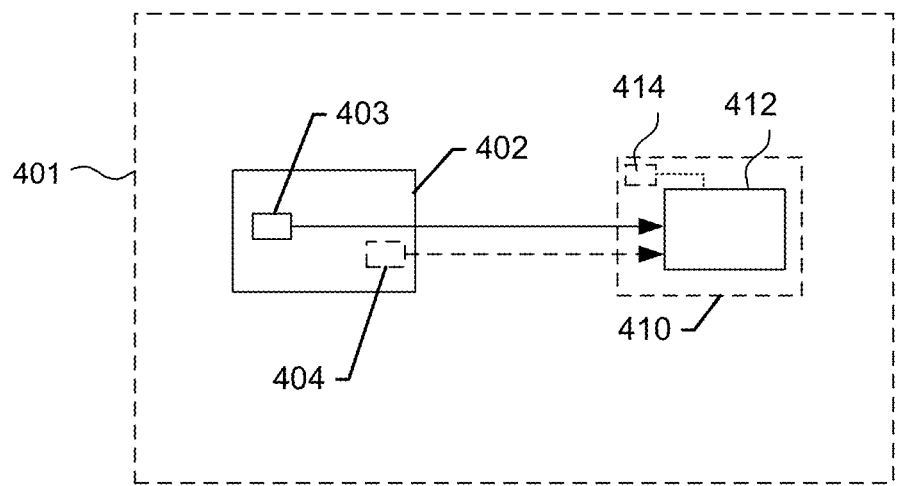
FIG. 4 shows a schematic drawing of an endoscope system according to an embodiment of the present disclosure.

FIG. 4 shows a schematic drawing of an embodiment of an endoscope system, denoted by numeral 401, comprising an endoscope 402 communicatively coupled to a monitor 410. The endoscope 402 includes a camera 403 and an enhancement level selector 404. The monitor 410 includes an image processor 412, as disclosed in relation to the second aspect of the disclosure and/or the third aspect of the disclosure, and a enhancement level selector 414. The camera 403 is operationally connectable to the image processor 412, which is configured to receive a video enhancement signal resulting from actuation of the enhancement level selectors and to enhance the video based on the signal. In this embodiment, the image processor 412 is integrated in the monitor 410, which includes a display screen configured to display the enhanced images. The video enhancement signal represents a value of a user parameter, or second parameter, for controlling the strength of the enhancements. One or the other of the enhancement level selectors may be omitted. The enhancement level selector 404 may be identical to the enhancement level selector 118 and the enhancement level selector 414 may be identical to the enhancement level selector 206.

Figure 5:
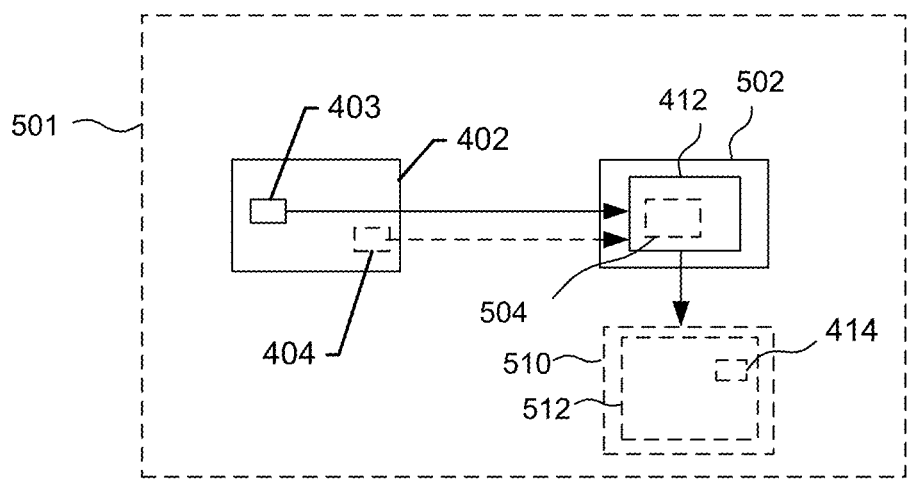
FIG. 5 shows a schematic drawing of an endoscope system according to an embodiment of the present disclosure.

FIG. 5 shows another embodiment of an endoscope system, denoted by numeral 501, including the endoscope 402 and the image processor 412, as disclosed in relation to the second aspect of the disclosure and/or the third aspect of the disclosure. The endoscope system 501 differs from the endoscope system 401 in that the image processor 412 is not integrated with the monitor, depicted by numeral 510. Instead, the image processor 412 is contained in a housing 502. The image processor 412 may comprise processing instructions, illustratively image processing logic 504, and optionally hardware, described further below, to receive user inputs indicative of the enhancement level. The housing 502 includes communication ports to receive the connector from the endoscope 402 and includes a video output port to output video signals to display the images with the display screen 512 of the monitor 510. The video output port may be an HDMI port.

The GUI may be provided by GUI logic. The GUI logic may include instructions to generate the enhancement level control, e.g. a selector of a value of a user parameter. Where the images are displayed in a display screen of a monitor, such as a portable monitor with a touch-screen, the user may engage the GUI by touch. The GUI may present in a first panel on the display screen a small version of live images provided by a first videoscope and in a second panel a large version of the live images provided by a second videoscope. A third panel may be provided in which the GUI may present various icons/control objects corresponding to actions selectable by the user with any of the above-described user input devices, to for example store a copy of a live image, store a portion of video corresponding to live images, invert the views, turn the enhancement features on and off, and select the level of enhancement.

Where the images are displayed in the image processor that does not include a display screen, for example, the image processor may include a user interface such as a wireless interface operable to receive user inputs via a mouse, keyboard, or other physical user input devices. Example wireless interfaces include Bluetooth and Zigbee controllers. The user interface may also comprise a USB port to receive a USB connector including the wireless interface or a USB connector of a wired user input device. Thus, the image processor provides for flexibility in receiving user inputs via various user input devices, regardless whether a display screen is integrated therewith. The term "logic" as used herein includes software and/or firmware executing on one or more programmable processing devices, application-specific integrated circuits, field-programmable gate arrays, digital signal processors, hardwired logic, or combinations thereof. Therefore, in accordance with the embodiments, various logic may be implemented in any appropriate fashion and would remain in accordance with the embodiments herein disclosed. Logic may comprise processing instructions embedded in non-transitory machine-readable media (e.g. memory).

The image processor includes medical device interfaces including connectors operable to receive the plugs of the videoscope's cables and to receive image data therefrom as disclosed above with reference to FIGS. 4 and 5. Image data may be referred to as "live images" or "live video" if they are received substantially in real-time from the videoscopes. The live video comprises a plurality of frames, each of which can be referred to as an "image." The image processor also includes the GUI logic and processing logic configured to implement the image enhancement methods described herein.

FIG. 6 shows a flowchart of an embodiment of a method of enhancing the visibility of blood vessels in a color image captured by a camera of a videoscope, such as endoscopes 100, 402. The method may be performed by the processing logic of the image processor. Shown is one color image 601 having a plurality of color channels. In this embodiment the color image 601 is coded in a RGB color space. In the first step, the color image 601 is split in the red color channel 602, the green color channel 603, and the blue color channel 604. One or more of the color channels 602, 603, 604 may be normalized as described below. Preferably, at least the red color channel is normalized. Next for each pixel, a value of a first sub parameter is created by subtracting 605 data obtained from the green color channel 603 (e.g. the green intensity value) from data obtained from the red color channel 602 (e.g. the red intensity value). This results in a first sub parameter image 607. Correspondingly, for each pixel, a value of a second sub parameter is created by subtracting 606 data obtained from the blue color channel 604 (e.g. the blue intensity value) from data obtained from the red color channel 602 (e.g. the red intensity value). This results in a second sub parameter image 608. Then, for each pixel, a value of a first parameter is created by calculating an average 609 of the value of the first sub parameter and the value of the second sub parameter. This results in a first parameter image 610. The first parameter has at least three possible values e.g. at least 8, 16, 32, 64, 128, 256 possible values. The first parameter image 610 shows regions in the color image 601 where the intensity in the red spectrum relative to the total intensity is high. This has shown to be a reliable indicator of blood vessels, because due to higher absorption of blue and green by the blood vessels, the total intensity in the area of the blood vessels is lower than in surrounding areas. Finally, the first parameter image 610 is subtracted from the base image to alter 611 the color image 601 creating an altered or enhanced image 612, wherein the strength of the alteration is dependent on the value of the first parameter. Optionally, a value of a user parameter 613 may be used to control the strength of the alteration, i.e. so that the strength of the alteration is dependent on the value of the first parameter and the value of the user parameter.

As an example, for each pixel, the value of the first parameter may be subtracted from the value of each color channel in the color image 601. This will have the effect that the blood vessels will become darker and the remaining parts of the image will remain substantially unchanged or become slightly darker. However, the colors will be left substantially unaffected. The overall intensity of the altered image 612 may be adjusted so that the intensity of the areas of the altered image 612 without blood vessels will have an intensity substantially matching the intensity of the corresponding areas in the original color image 601. For example, pixels having a small difference from the mean intensity of the first image (calibration pixels) could be considered to not have blood vessels, and the average intensity of these pixels in the base image could be used to calibrate the intensity of the altered image, such that the intensity of the altered image is changed until the average intensity of the calibration pixels in the altered image matches the average in the base image. The value of the user parameter may be a value between 0 and 1 that is used to scale the first parameter image e.g. by multiplying the first parameter image with the value of the user parameter, and then use the scaled first parameter image to subtract from the value of each color channel in the color image 601 as described above.

FIG. 7 shows a flowchart of another embodiment of the method of enhancing the visibility of blood vessels in a color image captured by an image capturing device of a medical device, e.g. a videoscope. The method may be performed by the processing logic of the image processor. The method may be performed by the processing logic of the image processor. Shown is a single color image 701 having a plurality of color channels. In this embodiment the color image 701 is coded in a RGB color space. In the first step, the color image 701 is split in the red color channel 702, the green color channel 703, and the blue color channel 704. Next, the red color channel 702 is low pass filtered 705 creating a low pass filtered red color channel 708, the green color channel 703 is low pass filtered 706 creating a low pass filtered green color channel 709, and the blue color channel is low pass filtered 707 creating a low pass filtered blue color channel 710. The low pass filtered color channels 708-710 show local averages for each pixel. Next, the low pass filtered red color channel 708 is used to normalize 711 the red color channel 702 creating a normalized red color channel 714, the low pass filtered green color channel 709 is used to normalize 712 the green color channel 703 creating a normalized green color channel 715, and the low pass filtered blue color channel 710 is used to normalize 714 the blue color channel 704 creating a normalized blue color channel 716. Normalization may be performed by dividing the color channel by the respective low pass filtered color channel. For example, dividing the red component image by the red pass filtered red component image.

Then, the normalized color channels 714-716 are processed together 718 to create a first parameter image 720 indicative of the intensity in the red spectrum relative to the total intensity. The normalized color channels 714-716 may be processed together 718 to create the first parameter image 720 in the same way as the color channels 602-604 in FIG. 6 are processed together to create the first parameter image 610. Next, the red, green, and blue color channel 702-704 are processed together to determine a value of a second parameter indicative of the intensity of each pixel e.g. by summing the red, green, and blue color channel 702-704, creating a second parameter image 719. Next, the first parameter image 720 and the second parameter image 719 are processed together 721 to create an alteration parameter image 722. This may be done by per pixel multiplying the first parameter image 720 with the second parameter image 719. Finally, the alteration parameter image 722 is used to alter 723 the color image 701 creating an altered or enhanced image 724, wherein the strength of the alteration is dependent on the value of the alteration parameter image 722. In one variation, the alteration comprises subtracting the alteration parameter image 722 from at least one color channel of the color image 701, preferably the red channel, creating an altered or enhanced image 724. In another variation, the alteration comprises subtracting the alteration parameter image 722 from all three channel of the color image 701, creating an altered or enhanced image 724.

FIG. 8a shows a color image of an internal cavity before the visibility of the blood vessels have been enhanced and FIG. 8b shows the color image after the visibility of the blood vessels have been enhanced according to an embodiment of the disclosure. It can be seen that the blood vessels are more clear in the image in FIG. 8b while the presentation of the other tissue types are substantially unchanged. This will allow the medical personnel to effectively examine both the vascular structures and the other areas of the internal cavity for pathological changes.

Figure 9:
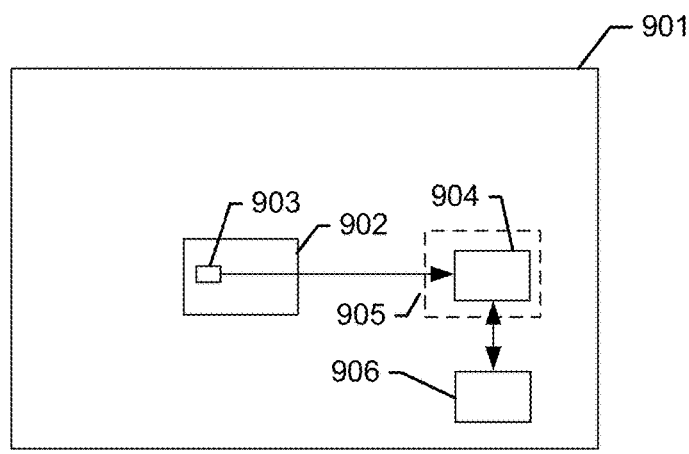
FIG. 9 shows a schematic drawing of a visualization system according to an embodiment of the disclosure.

FIG. 9 shows a schematic drawing of an endoscope system 901 according to an embodiment of the disclosure. The endoscope system 901 comprises an endoscope 902, a first image processor 904, and a second image processor 906, where both the first image processor 904 and the second image processor 906 have a processing unit. The endoscope 902 has an image capturing device 903 and the processing unit of the first image processor 904 is operationally connectable to the image capturing device of the endoscope 903. In this embodiment, the first image processor 904 is integrated in a monitor 905 and the processing unit of the second image processor 906 is directly operationally connectable to the processing unit of the first image processor 904 and indirectly operationally connectable to the image capturing device of the endoscope 903 via the first image processor 904. In this embodiment the processing unit of the first image processor 904 is configured to generate an image adapted for computer image analysis by processing a color image having a plurality of color channels recorded by the image capturing device 903, the color image has a plurality of pixels wherein the processing of the color image comprises for at least some of said plurality of pixels the steps of: (a) process data obtained from a first color channel together with data obtained from a second color channel to determine a value of a first parameter indicative of the intensity in the red spectrum relative to the total intensity of said pixel; (b) using said value of said first parameter to create a pixel value of the image adapted for computer image analysis.

The image adapted for computer image analysis is forwarded to the second image processor 906 where the image adapted for computer analysis is processed using a machine learning data architecture trained to identify potential pathological vascular structures in such images. Identification of pathological vascular structures is identified by comparing image characteristics to a library of characteristics identified in training images.

The second image processing unit 906 may be arranged in proximity of the first image processor 904, where the first and second image processor 904, 906 communicate directly or via a local network. Alternatively, the second image processor may be arranged remotely from the first image processor and communicate via a WAN, such as the internet. The output from the machine learning data architecture may be a notification provided to the first image processor 904. The notification may simply specify that a potential pathological vascular structure has been identified. However, the notification may also indicate the type of pathology and/or the location in the image. If the notification specifies the location of the potential pathology, then the monitor 905 may be configured to highlight the part of the image where the potential pathology has been identified. The image adapted for computer analysis may more clearly show the vascular structures (compared to the original color image) thereby making it easier for the machine learning data architecture to identify potential pathological vascular structures. Examples of images adapted for computer analysis are (with reference to the FIG. 7 embodiment) the altered image 724, the first parameter image 720, and the alteration parameter image 722.

FIG. 10 illustrates how the strength of the enhancement may be controlled using a touch-screen according to an embodiment. FIG. 10, a, shows an image 1001 recorded by an image capturing device e.g. an image capturing device of an endoscope. Blood vessels 1002 in the image 1001 are not enhanced. The image 1001 may be processed to improve its overall quality e.g. to correct colors, set contrast, brightness etc. A part of the touch-screen is used to display a user interface configured to turn on enhancement of blood vessels and control the strength of the enhancement. The user interface may comprise a button 1003, configured to allow a user to turn the enhancement of the blood vessels on/off. The user interface may comprise one or more enhancement level selectors, e.g. buttons 1004, 1005, configured to allow a user to control the strength of the enhancement. The user interface may comprise an enhancement indicator 1006 for indicating the selected strength of the enhancement. The enhancement indicator 1006 may further function as an enhancement level selectors, e.g. a slider, whereby a user may slide the indicator 1006 to a desired position to select a particular strength of the enhancement. FIG. 10, a, shows an un-enhanced image, FIG. 10, b, shows an image enhanced with a medium strength, FIG. 10, c, shows an image enhanced with a high strength, and FIG. 10, d, shows an image enhanced with a low strength. A visual identifier 1007 such, as a symbol or icon, may be inserted into the enhanced image to show to the user that the image has been enhanced. The touch-screen may show live images, where the user interface is configured to turn on enhancement of blood vessels and control the strength of the enhancement on the live images. The touch-screen may also show one or more recorded images, where the user interface is configured to turn on/off enhancement of blood vessels and control the strength of the enhancement on the one or more recorded images.

FIG. 11 shows a flowchart of another embodiment of a method of enhancing the visibility of blood vessels in a color image. The color image has a plurality of color channels and a plurality of pixels, wherein the method comprises for at least some of the plurality of pixels the steps of: 1101 processing data obtained from a first color channel together with data obtained from a second color channel to determine a value of a first parameter indicative of the intensity in the red spectrum relative to the total intensity of the pixel; 1102 receiving user input comprising a first value of a user parameter; and 1103 using said value of said first parameter and said first value of a user parameter to alter said pixel, the first value of the user parameter being based on the user input, and wherein the strength of the alteration is dependent on both the value of said first parameter and the first value of said user parameter.

FIG. 12 shows a flowchart of a method of changing the enhancement of a recorded enhanced image according to an embodiment of the disclosure. The method comprises: 1201 storing a first enhanced image on the storage unit; 1202 storing on the storage unit an original un-enhanced image or image data capable of re-creating the original un-enhanced image based on the stored enhanced image; 1203 obtaining a second value of a user parameter based on user input; and 1204 creating a second enhanced image based on the original un-enhanced image and the second value of the user parameter, the second enhanced image being enhanced with a different strength than the first enhanced image.

The second enhanced image can also be created by saving intermediate images obtained during the processing of the base image to obtain the first enhanced image. Using intermediate images saves processing steps in that normalization and other processing does not have to be duplicated. The intermediate images are those that suffice to create an enhanced image prior to using the value of the user parameter. These include, for example, the first parameter image, the first intensity difference image, the LP filtered color images, or the normalized color images. If the base color image is used, the additional processing could simply be to use the first parameter image with the user value to create the second enhanced image. This reduces processing at the expense of saving an additional image. If the first enhanced image is saved, further processing includes undoing the first enhancement and then applying the second user value.

Additional/Alternative embodiments: Some of the embodiments above, the embodiments below, and some of the appended claims are described with reference to endoscopes or blood vessels. It should be understood, however, that the disclosed features are applicable to any videoscope to detect colored masses in images and that the reference to blood vessels is to illustrate a particularly useful application of the invention, without limiting the invention to the enhancement of images including vessels.

1. A method of enhancing the visibility of blood vessels in a colour image captured by an image capturing device of a medical device, said colour image having a plurality of colour channels and having a plurality of pixels, wherein said method comprises for at least some of said plurality of pixels the steps of:

(a) processing data obtained from a first colour channel together with data obtained from a second colour channel to determine a value of a first parameter indicative of the intensity in the first color channel relative to the total intensity of said pixel;

(b) using said value of said first parameter to alter said pixel, wherein said first parameter has at least three possible values, and wherein the strength of the alteration is dependent on the value of said first parameter 2. A method according to embodiment 1, wherein step (a) comprises: processing data obtained from a first colour channel together with data obtained from a second colour channel and data obtained from a third colour channel to determine a value of said first parameter.

3. A method according to embodiment 2, wherein said data obtained from the first colour channel is processed together with said data obtained from the second colour channel to create a value of a first sub parameter, said data obtained from said first colour channel is processed together with said data obtained from said third colour channel to create a value of a second sub parameter, and wherein said value of said first sub parameter is processed together with said value of said second sub parameter to create said value of said first parameter.

4. A method according to embodiment 3, wherein both said value of said first sub parameter and said value of said second sub parameter are indicative of the intensity in the first color channel relative to the total intensity of said pixel.

5. A method according to any one of embodiments 1 to 4, wherein step (a) comprises subtracting said data obtained from the second colour channel from said data obtained from the first colour channel.

6. A method according to any one of embodiments 1 to 5, wherein parts of the colour image having no blood vessels are substantially unaltered and displayed with normal colours.

7. A method according to any one of embodiments 1 to 6, wherein said method further comprises: determining a value of a second parameter indicative of the intensity of said pixel and wherein said value of said first parameter together with said value of said second parameter is used to alter said pixel.

8. A method according to any one of embodiments 1 to 7, wherein said plurality of colour channels are normalized prior to being processed together.

9. A method according to embodiment 8, wherein a low pass filtered image is created for each of said plurality of colour channels indicating a local average for each pixel, and wherein each colour channel is normalized using its low pass filtered image.

10. A method according to any one of embodiments 1 to 9, wherein a value of a third parameter is created based on user input, and wherein the alteration is dependent on both said value of said first parameter and said value of said third parameter, whereby the user may control the strength of the alteration.

11. A method according to any one of embodiments 1 to 10, wherein a high value of the first parameter indicates a high intensity in the first color channel relative to the total intensity of said pixel and a low value of the first parameter indicates a low intensity in the first color channel relative to the total intensity of said pixel.

12. A method according to embodiment 11, wherein values of the first parameter that are among the 50% highest of all possible values results in alterations that are more significant than the alterations that results from values of the first parameter that are among the 50% lowest of all possible values.

13. A method according to embodiments 11 or 12, wherein for at least 50% of the possible values of said first parameter an increase in the value of the first parameter results in an increase in the strength of the alteration.

14. A method according to any one of embodiments 1 to 13. wherein the alteration of said pixel is independent of the intensity in the green spectrum relative to the blue spectrum.

A method according to any one of embodiments 1 to 14, wherein the first color channel corresponds to the red spectrum.

15. An image processing device for enhancing the visibility of blood vessels in a colour image, said image processing device comprising a processing unit operationally connectable to an image capturing device of a medical device, wherein said processing unit is configured to receive a colour image having a plurality of colour channels from said image capturing device, said colour image has a plurality of pixels and wherein said processing unit further is configured to for at least some of said plurality of pixels perform the steps of:

(a) process data obtained from a first colour channel together with data obtained from a second colour channel to determine a value of a first parameter indicative of the intensity in the first color channel relative to the total intensity of said pixel;

(b) using said value of said first parameter to alter said pixel, wherein said first parameter has at least three possible values, and wherein the strength of the alteration is dependent on the value of said first parameter.

16. An image processing device according to embodiment 15, wherein step (a) comprises: processing data obtained from a first colour channel together with data obtained from a second colour channel and data obtained from a third colour channel to determine a value of said first parameter.

17. An image processing device according to embodiment 16, wherein said data obtained from the first colour channel is processed together with said data obtained from the second colour channel to create a value of a first sub parameter, said data obtained from said first colour channel is processed together with said data obtained from said third colour channel to create a value of a second sub parameter, and wherein said value of said first sub parameter is processed together with said value of said second sub parameter to create said value of said first parameter.

18. An image processing device according to embodiment 17, wherein both said value of said first sub parameter and said value of said second sub parameter are indicative of the intensity in the first color channel relative to the total intensity of said pixel.

19. An image processing device according to any one of embodiments 16 to 18, wherein step (a) comprises subtracting said data obtained from the second colour channel from said data obtained from the first colour channel.

20. An image processing device according to any one of embodiments 15 to 19, wherein parts of the colour image having no blood vessels are substantially unaltered and displayed with normal colours.

21. An image processing device according to any one of embodiments 15 to 20, wherein the processing unit is further configured to perform the step of:

determining a value of a second parameter indicative of the intensity of said pixel and wherein said value of said first parameter together with said value of said second parameter is used to alter said pixel.

22. An image processing device according to any one of embodiments 15 to 21, wherein said plurality of colour channels are normalized prior to being processed together.

23. An image processing device according to embodiment 22, wherein a low pass filtered image is created for each of said plurality of colour channels indicating a local average for each pixel, and wherein each colour channel is normalized using its low pass filtered image.

24. An image processing device according to any one of embodiments 15 to 23, wherein said image processing device is operationally connectable to an input unit for receiving user input and further configured to receive a user selected value of a third parameter from said input unit and wherein the alteration is dependent on both said value of said first parameter and said value of said third parameter, whereby the user may control the strength of the alteration.

25. An image processing device according to any one of embodiments 15 to 24, wherein a high value of the first parameter indicates a high intensity in the first color channel relative to the total intensity of said pixel and a low value of the first parameter indicates a low intensity in the first color channel relative to the total intensity of said pixel.

26. An image processing device according to embodiment 25, wherein values of the first parameter that are among the 50% highest of all possible values results in alterations that are more significant than the alterations that results from values of the first parameter that are among the 50% lowest of all possible values.

27. An image processing device according to embodiments 25 or 26, wherein for at least 50% of the possible values of said first parameter an increase in the value of the first parameter results in an increase in the strength of the alteration.

28. An image processing device according to any one of embodiments 15 to 27, wherein the first color channel corresponds with the red spectrum, and wherein the alteration of said pixel is independent of the intensity in the green spectrum relative to the blue spectrum.

29. An image processing device for identifying potential pathological vascular structures, said image processing device comprising a processing unit operationally connectable to an image capturing device of a medical device, wherein said processing unit is configured to process an image adapted for computer image analysis using a machine learning data architecture trained to identify potential pathological vascular structures in such images, wherein said image adapted for computer analysis is generated by processing a colour image having a plurality of colour channels recorded by said image capturing device, said colour image has a plurality of pixels wherein the processing of said colour image comprises for at least some of said plurality of pixels the steps of:

(a) process data obtained from a first colour channel together with data obtained from a second colour channel to determine a value of a first parameter indicative of the intensity in the first color channel relative to the total intensity of said pixel;

(b) using said value of said first parameter to create a pixel value of the image adapted for computer image analysis.

30. An image processing device according to embodiment 29, wherein said machine learning data architecture is a supervised machine learning architecture provided with a training data set of images created by steps a) and b), where a first subset of images of said training data set show a pathological vascular structure and a second subset of images of said training data set show a healthy vascular structure.

31. An image processing device according to embodiment 30, wherein the training data set comprises a plurality of images showing vascular structures of tumours.

32. An image processing device according to any one of embodiments 29 to 31, wherein the pixel values of the image adapted for computer image analysis corresponds to the value of the first parameter optionally multiplied with a weight value derived from said colour image; or the pixel values of the image adapted for computer image analysis is an altered pixel from said colour image altered using the value of said first parameter and wherein the strength of the alteration is dependent on the value of said first parameter.

33. An image processing device according to any one of embodiments 29 to 32, wherein the machine learning data architecture is an artificial neural network such as a deep structured learning architecture.

34. An image processing device according to any one of embodiments 29 to 33, wherein the processing unit is directly operationally connectable to the image capturing device and configured to receive the colour image and perform steps a) and b) to create the image adapted for computer image analysis.

35. An image processing device according to embodiment 34, wherein the processing unit is indirectly operationally connectable to the image capturing device via another image processing device, wherein said image processing device is configured to receive said image adapted for computer image analysis from said another image processing device, said another image processing device being configured to receive the colour image and perform steps a) and b) to create the image adapted for computer image analysis.

36. An image processing device according to embodiments 15 to 35, wherein the first color channel corresponds to the red spectrum.

37. A display unit for displaying images obtained by an image capturing device of a medical device, wherein said display unit comprises an image processing device according to any one of embodiments 15 to 36.

38. An endoscope system comprising an endoscope and an image processing device according to any one of embodiments 15 to 36, wherein said endoscope has an image capturing device and said processing unit of said image processing device is operationally connectable to said image capturing device of said endoscope.

39. An endoscope system according to embodiment 38, wherein the endoscope system further comprises a display unit according to embodiment 37, wherein said display unit is operationally connectable to said image capturing device of said endoscope and configured display said captured images.

40. A computer program product comprising program code means adapted to cause a data processing system to perform the steps of the method according to any one of embodiments 1 to 14, when said program code means are executed on the data processing system.

41. A computer product as in claim 40, wherein the first color channel corresponds with the red spectrum.

42. A computer program product according to embodiments 40 or 41, wherein said computer program product comprises a non-transitory computer-readable medium having stored thereon the program code means.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

References to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment.

The scope of the invention is to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

We claim:

1. A method of enhancing visibility of blood vessels, the method comprising:
   processing pixel data from a red color channel of a color image together with pixel data from a green or a blue color channel of the color image to determine values of a first parameter for pixels of the color image;
   receiving, from a user interface actuated by a user, an enhancement level signal indicative of a first value of a user parameter; and
   generating an enhanced image by changing intensities of the pixels of the color image using the first value of the user parameter and the values of the first parameter corresponding to the pixels,
   wherein the first parameter comprises a difference between intensities of a pixel in the red channel and the green or the blue channel, and
   wherein the processing includes obtaining a red-green intensity difference as a difference between intensities of the pixel in the red channel and the green channel, and obtaining a red-blue intensity difference as a difference between intensities of the pixel in the red channel and the blue channel, and wherein the value of the first parameter of the pixel is based on an average of the red-green intensity difference and the red-blue intensity difference.

2. The method of claim 1, further comprising, prior to obtaining the red-green intensity difference and the red-blue intensity difference, normalizing the intensities of the pixels in the red channel, the green channel, and the blue channel.

3. The method of claim 1, wherein using the first value of the user parameter includes multiplying the value of the first parameter by the first value of the user parameter before generating the enhanced image.

4. A method of enhancing visibility of blood vessels, the method comprising:
   processing pixel data from a red color channel of a color image together with pixel data from a green or a blue color channel of the color image to determine values of a first parameter for pixels of the color image;
   receiving, from a user interface actuated by a user, an enhancement level signal indicative of a first value of a user parameter; and
   generating an enhanced image by changing intensities of the pixels of the color image using the first value of the user parameter and the values of the first parameter corresponding to the pixels, wherein the first parameter comprises a difference between intensities of a pixel in the red channel and the green or the blue channel, and wherein the processing includes:

low-pass (LP) filtering a red channel image of the color image to create a LP red image;

dividing the red channel image by the LP red image to create a normalized red image; and creating a first intensity difference image as a difference between the normalized red image and an image based on a green or blue channel image of the color image.

5. The method of claim 4, wherein generating an enhanced image includes subtracting the first intensity difference image from the red channel image.

6. The method of claim 4, wherein generating an enhanced image includes subtracting the first intensity difference image from the color image.

7. The method of claim 4, wherein the processing further includes:

LP filtering a green or blue channel image of the color image to create a LP green or blue image;

dividing the green or blue channel image by the LP green or blue image to create a normalized green or blue image; and wherein the image based on a green or blue channel image of the color image comprises the normalized green or blue image.

8. The method of claim 7, wherein the green or blue channel image is the green channel image, and wherein the processing further includes:

LP filtering a blue channel image of the color image to obtain a LP blue image;

dividing the blue channel image by the LP blue image to create a normalized blue image;

obtaining a second intensity difference image as a difference between the normalized red image and the normalized blue image; and averaging the first intensity difference image and the second intensity difference image to create the first parameter image.

9. The method of claim 8, wherein generating an enhanced image includes subtracting the first parameter image from the red channel image, from the green channel image, and from the blue channel image.

10. The method of claim 8, wherein generating an enhanced image includes summing the red channel image with the green channel image and the blue channel image to create a second parameter image, multiplying the first parameter image and the second parameter image to create an alteration parameter image, and subtracting the alteration parameter image from the red channel image, the green channel image, and the blue channel image, to generate the enhanced image.

11. The method of claim 10, wherein using the first value of the user parameter includes, before generating the enhanced image, multiplying the first parameter image or the second parameter image or the alteration parameter image by the first value of the user parameter.

12. The method of claim 1, further comprising:

storing an image based on the enhanced image or the color image;

receiving a second enhancement level signal indicative of a second value of the user parameter, the second value being different than the first value;

retrieving the stored image; and creating a second enhanced image based on the stored image and the second value of the user parameter.

13. The method of claim 4, further comprising:

storing an image based on the enhanced image or the original image;

storing the first parameter image or the first intensity difference image;

receiving a second enhancement level signal indicative of a second value of the user parameter, the second value being different than the first value;

retrieving the stored image and the first parameter image or the first intensity difference image; and creating a second enhanced image based on the stored image, the second value of the user parameter, and the first parameter image or the first intensity difference image.

14. The method of claim 1, further comprising processing the enhanced image with a machine learning data architure trained with a library of health and pathological structures to identify a pathological structure in the enhanced image.

15. An image processor for enhancing visibility of blood vessels, the image processor comprising:

a videoscope interface including a connection port adapted to receive a connector of a videoscope having a camera operable to generate color image data representative of a color image having a red color channel, a blue color channel, and a green color channel;

graphical user interface (GUI) logic operable to present a GUI including an enhancement level control to generate a first value of a user parameter;

image processing logic structured to, when executed, implement a method to generate an enhanced image from the color image data, the method comprising:

receiving the color image data generated by the videoscope;

processing pixel data from the red color channel with pixel data from the green or the blue color channel to determine values of a first parameter for pixels of the color image; and generating the enhanced image by changing intensities of the pixels of the color image using the first value of the user parameter and the values of the first parameters corresponding to the pixel; and a housing at least partially enclosing the videoscope interface, the GUI logic, and the image processing logic, wherein the processing includes obtaining a red-green intensity difference as a difference between intensities of a pixel in the red channel and the green channel, and obtaining a red-blue intensity difference as a difference between intensities of the pixel in the red channel and the blue channel, and wherein the value of the first parameter of the pixel comprises an average of the red-green intensity difference and the red blue intensity difference.

16. The image processor of claim 15, further comprising a display module including a display screen, wherein the GUI logic presents the enhanced image and the enhancement level control with the display.

17. The image processor of claim 15, wherein the processing further comprises:

low-pass (LP) filtering a red channel image of the color image to obtain a LP red image;

LP filtering a green channel image of the color image to obtain a LP green image;

LP filtering a blue channel image of the color image to obtain a LP blue image;

dividing the red channel image by the LP red image to create a normalized red image;

dividing the green channel image by the LP green image to create a normalized green image;

dividing the blue channel image by the LP blue image to create a normalized blue image;

obtaining a red-green intensity difference image as a difference between the normalized red image and the normalized green image;

obtaining a red-blue intensity difference image as a difference between the normalized red image and the normalized blue image; and averaging the red-blue intensity difference image and the red-green intensity difference image to create a first parameter image.

18. An image processor for enhancing visibility of blood vessels, the image processor comprising:

a videoscope interface including a connection port adapted to receive a connector of a videoscope having a camera operable to generate color image data representative of a color image having a red color channel, a blue color channel, and a green color channel;

image processing logic structured to, when executed, implement a method to generate an enhanced image from the color image data, the method comprising:

receiving the color image data generated by the videoscope;

processing pixel data from the red color channel with pixel data from the green or the blue color channel to determine values of a first parameter for pixels of the color image, wherein the processing includes obtaining a red-green intensity difference as a difference between intensities of a pixel in the red channel and the green channel and obtaining a red-blue intensity difference as a difference between intensities of the pixel in the red channel and the blue channel, wherein the value of the first parameter of the pixel comprises an average of the red-green intensity difference and the red-blue intensity difference; and generating the enhanced image by changing intensities of the pixels of the color image using the values of the first parameters corresponding to the pixel; and a housing at least partially enclosing the videoscope interface and the image processing logic.

19. The image processor of claim 18, further comprising a display module including a display screen, wherein the GUI logic presents the enhanced image with the display screen.

20. The image processor of claim 18, wherein the processing includes, before creating the red-green intensity difference and the red-blue intensity difference, normalizing the pixel data from the red color channel, the green color channel, and the blue color channel.

* * * * *

UNITED STATES PATENT AND TRADEMARK OFFICE
CERTIFICATE OF CORRECTION

PATENT NO. : 11,074,690 B2  
APPLICATION NO. : 16/811927  
DATED : July 27, 2021  
INVENTOR(S) : Jorgensen et al.

Page 1 of 1

It is certified that error appears in the above-identified patent and that said Letters Patent is hereby corrected as shown below:

On the Title Page

Item (72), Line 2, change "Finn Sønnenborg" to --Finn Sonnenborg--

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*